(12) United States Patent
Eytan (10) Patent No.: US 12,193,646 B2
(45) Date of Patent: Jan. 14, 2025

(54) CHIMNEY AND FLANGE DESIGN FOR CAMERA MODULE

(71) Applicant: Mobileye Vision Technologies Ltd., Jerusalem (IL)

(72) Inventor: Ori Eytan, Jerusalem (IL)

(73) Assignee: Mobileye Vision Technologies Ltd., Jerusalem (IL)

( * ) Notice: Subject to any disclaimer, the term of this patent is extended or adjusted under 35 U.S.C. 154(b) by 434 days.

(21) Appl. No.: 17/617,186

(22) PCT Filed: Jun. 23, 2020

(86) PCT No.: PCT/IB2020/000498
§ 371 (c)(1),
(2) Date: Dec. 7, 2021

(87) PCT Pub. No.: WO2021/001684
PCT Pub. Date: Jan. 7, 2021

(65) Prior Publication Data
US 2022/0296088 A1    Sep. 22, 2022

Related U.S. Application Data

(60) Provisional application No. 62/870,279, filed on Jul. 3, 2019.

(51) Int. Cl.
*A61B 1/05*    (2006.01)
*A61B 1/00*    (2006.01)
*G02B 7/00*    (2021.01)

(52) U.S. Cl.
CPC ............ *A61B 1/05* (2013.01); *A61B 1/00096* (2013.01); *G02B 7/005* (2013.01)

(58) Field of Classification Search
CPC ... A61B 1/05; A61B 1/00096; A61B 1/00188; G02B 7/005; G02B 7/023; G02B 7/003; G02B 7/025; G02B 13/001; G02B 13/16
USPC ......................................... 348/349
See application file for complete search history.

(56) References Cited

U.S. PATENT DOCUMENTS

2008/0131110 A1   6/2008  Lee et al.
2016/0295081 A1*  10/2016  Graff ....................... G02B 7/028
2017/0048432 A1   2/2017  Campbell
(Continued)

FOREIGN PATENT DOCUMENTS

| CN | 200997010  | 12/2007 |
| CN | 208172400  | 11/2018 |
| JP | 2010137316 | 6/2010  |

(Continued)

OTHER PUBLICATIONS

"International Application Serial No. PCT/IB2020/000498, International Search Report mailed Sep. 18, 2020", 4 pgs.

(Continued)

*Primary Examiner* — Yogesh K Aggarwal
(74) *Attorney, Agent, or Firm* — Schwegman Lundberg & Woessner, P.A.

(57) ABSTRACT

A camera module assembly can include a chimney and a lens assembly. The chimney can include a distal portion having a substantially spherical profile. The lens assembly can include a lens barrel, an optical device, and a flange extending radially from the lens barrel, where the flange can be securable to the distal portion of the chimney.

20 Claims, 4 Drawing Sheets

(56) References Cited

U.S. PATENT DOCUMENTS

2017/0343831 A1    11/2017  Bakin et al.

FOREIGN PATENT DOCUMENTS

| KR | 101350395 | 1/2014 |
| TW | 201541956 | 11/2015 |
| WO | WO-2014054742 A1 | 4/2014 |
| WO | WO-2021001684 A1 | 1/2021 |

OTHER PUBLICATIONS

"International Application Serial No. PCT/IB2020/000498, Written Opinion mailed Sep. 18, 2020", 6 pgs.

"Chinese Application Serial No. 202080048581.X, Office Action mailed Dec. 26, 2023", w English Translation, 18 pgs.

\* cited by examiner

CHIMNEY AND FLANGE DESIGN FOR CAMERA MODULE

PRIORITY

This application is a U.S. National Stage Application under 35 U.S.C. 371 from International Application No. PCT/IB2020/000498, filed Jun. 23, 2020, and published as WO 2021/001684 on Jan. 7, 2021, which claims priority to U.S. Provisional Patent Application No. 62/870,279, filed Jul. 3, 2019, which are incorporated by reference herein in their entirety.

BACKGROUND

Digital image capture devices (cameras) are devices designed to capture an image and to produce a signal and often, ultimately, an electronic image based on the capture. Such devices often include a lens or optical device and a digital or electronic image sensor. Digital cameras can be used to capture single images or multiple images to create video files. Digital cameras capable of one or both functions are commonly found in many goods such mobile devices (phones and tablet computers) and automobiles. Due to the prevalence of such devices, digital cameras are produced in mass quantities around the world, where mass production of cameras often includes multiple manufacturing processes. One such process is a multi-step alignment process to help ensure clear images are captured by the sensor. As cameras increase in resolution, improved manufacturing and alignment of camera components can improve camera performance and reliability.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Camera technologies have improved greatly over the past decade. Applications of such technologies have become more prevalent, causing a demand for high quality, relatively low-price camera modules. One way to reduce the price of the camera modules is to use camera modules having an optical device that can have a misaligned optical axis. That is, the optical axis of the lens may not align with a mechanical axis of the optical device or the body that supports the optical device. In some circumstances, the optics-to-mechanics error is limited to about 0.5°. While helping to reduce cost, such deviation causes manufacturing difficulties because placement of the optical device with respect to an image sensor of the camera module is not repeatable or does not include identical steps between different lens assemblies. Further complicating manufacturing is that the optical device is often fixed with respect to the lens barrel (or housing) and lens flange.

A common solution for aligning the optical device with respect to the image sensor is to tilt the barrel and therefore the optical device to align the optical (or focal) axis of the optical device with the mechanical axis of the chimney and optimize the image quality created by the optical device onto the image sensor. This process can position a focal point of the optical device in a center (or focal point) of the image capture sensor. Once alignment is complete, the optical device is fixed with respect to the chimney using an adhesive or gluing process, where adhesive is applied between the lens flange and the chimney and then cured. However, most adhesives used to secure the optical device to the chimney shrink during processing of the adhesive, such as during the curing process. This shrinkage is a potential problem, for multiple reasons. First, if the adhesive gap (or thickness of the adhesive) is not uniform between the flange and the chimney, the optical device can be tilted with respect to the chimney and with respect to the image sensor, causing misalignment between the optical axis of the optical device and the mechanical axis of the chimney. Second, a non-constant gap induces a larger average gap relative to what it could be for constant gap. Such a large gap results in a relatively large and thick adhesive layer that is subjected to adhesive shrinkage variations that creates focus error by moving the focal point of the optical device with respect to the image sensor. Another reason is that the shrinkage effect is not always fully predictable and is typically not fully repeatable, therefore perfect pre-compensation for the shrinkage is not possible Therefore, to address these and other issues, this disclosure provides a chimney with a substantially spherical profile with a lens flange having a substantially spherical and substantially concentric (and therefore complimentary) shape. This design allows the lens assembly (and the flange) to be rotated (or tilted) about a center of rotation with respect to the chimney without affecting an adhesive gap between the chimney and the flange. This arrangement allows for the optical axis of the optical device to be aligned with the mechanical axis of the chimney while maintaining a substantially constant thickness of adhesive between the chimney and the flange around an adhesive area of the chimney. The constant thickness of adhesive can help minimize movement of the optical device with respect to the image capture sensor during the curing process (due to shrinkage), helping to improve image quality using relatively lower cost optical devices to help improve production yield.

For example, for a flange having a 22 millimeter (mm) flange diameter and having a lens tilt of 0.5 degrees, a resulting glue non-uniformity is about 0.2 mm thickness difference from one side to the other side. Such a difference in adhesive or glue uniformity can induce shrinkage uncertainty that cannot be pre-compensated for in practice, because the shrinkage process depends on many factors, including: thickness, surface angle, excessive glue that was rejected at the lower thickness side, etc. The arrangements discussed above can help to reduce or eliminate such a non-uniformity of a lens tilt of 0.5 degrees. In addition, this arrangement can also allow a camera design to be used that includes a smaller nominal flange to chimney gap, because it is not required to address tilt-induced proximity areas. It should be appreciated that other examples can be envisioned where the flange is of a different diameter and/or a different lens tilt is used, and where the glue non-uniformity is different than the numerical example given above.

The above discussion is intended to provide an overview of subject matter of the present patent application. It is not intended to provide an exclusive or exhaustive explanation of the invention. The description below is included to provide further information about the improved design.

Figure 1:
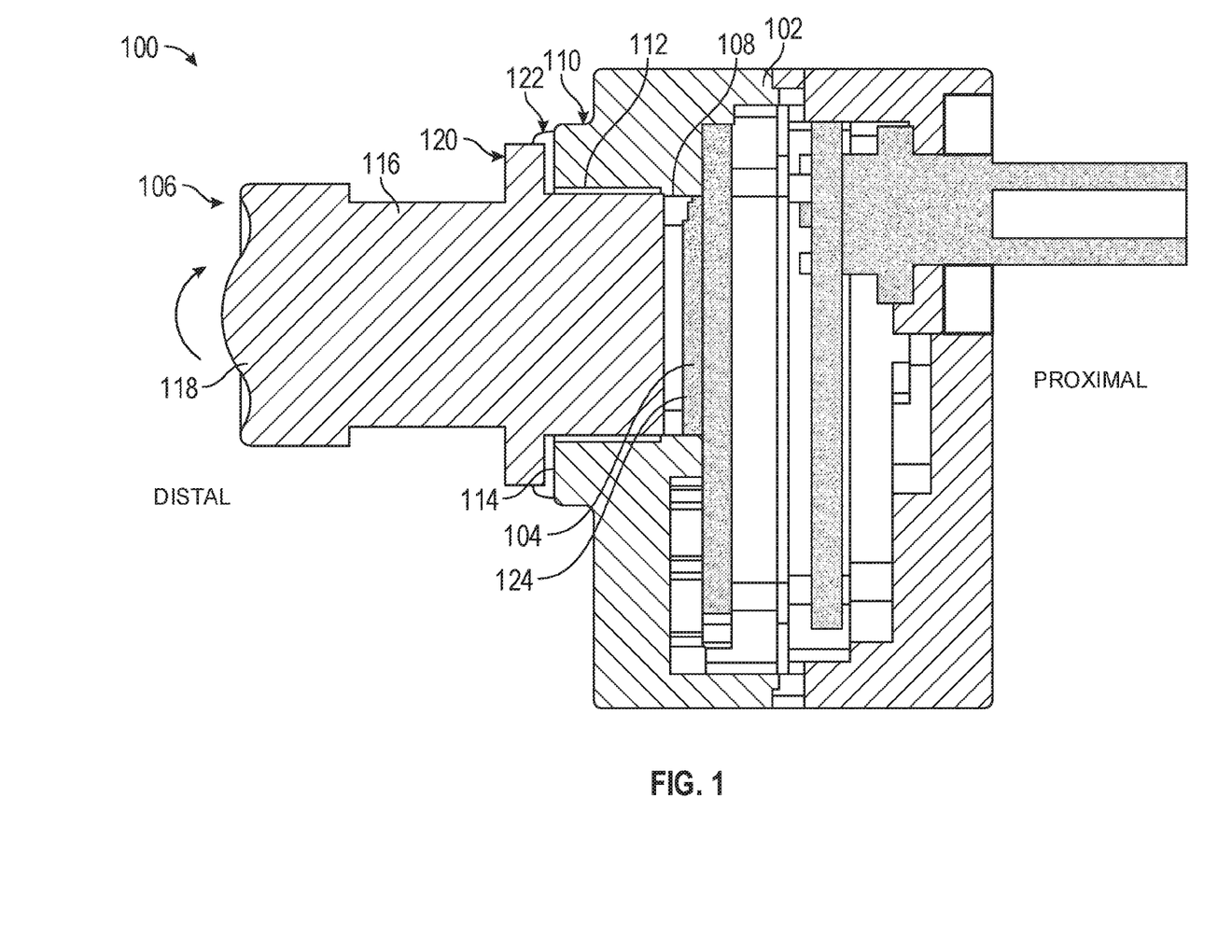
FIG. 1 illustrates a cross-sectional view of a camera module, in accordance with at least one example of this disclosure.

FIG. 1 illustrates a cross-sectional view of a camera module 100, in accordance with at least one example of this disclosure. The camera module 100 can include a body 102, an image capture sensor 104, and a lens assembly 106. The body 102 can include a cavity 108 and a chimney 110. The chimney 110 can include a chimney bore 112 and a distal portion 114. The lens assembly 106 can include a lens barrel 116, an optical part 118 (or optical parts 118 or optical device 118), and a flange 120. The camera module 100 can also include adhesive (or glue) 122. FIG. 1 also shows orientation indicators Proximal and Distal.

The body 102 can be a rigid or semi-rigid body comprised of materials such as one or more of metals, plastics, foams, elastomers, ceramics, composites, combinations thereof, or the like. The body 102 can be sized and shaped to be mounted to a machine (such as a vehicle), in some examples, or can be sized and shaped to be handheld, in other examples. The cavity 108 can be a cavity within the body 102 sized and shaped to receive and support one or more components therein, such as the image capture sensor 104.

The chimney 110 can be a portion of the body 102 extending distally from the body 102 and can include a chimney bore 112 extending through the chimney 110 and connected to the cavity 108. The chimney 110 can be generally cylindrical in shape and the chimney bore 112 can be sized to receive a portion of the lens assembly 106 therein to connect the lens assembly 106 to the body 102. The distal portion 114 of the chimney 110 can be sized and shaped to engage with the flange 120 of the lens assembly 106 and can be configured to receive the adhesive 122 thereon to secure the lens assembly 106 to the body 102. As discussed further below, in some examples, the distal portion 114 of the chimney 110 can be curved or substantially spherical where the chimney 110 engages the flange 120. The distal portion 114 can be spherical, such that the distal portion 114 has a spherical surface profile where the radius of each point of the surface of the distal portion 114 is equidistant from a center of the surface of the distal portion 114. The distal portion 114 can also be substantially spherical, such that the distal portion 114 has a curvature where every point of the surface of the distal portion 114 is not equidistant from the center. In such a case, the radius of each point can vary by up to 6 percent over an average radius. In another example where the distal portion 114 can be substantially spherical, the radius of each point can vary by up to 2 percent of an average radius.

The image capture sensor 104 can include an image plane 124 (e.g., film plane), which can be a plane of the imaging sensor. The image capture sensor 104 can include an active pixel sensor, a semiconductor charge-coupled device (CCD), a CMOS image sensor, or other imaging sensor configured to produce a signal based on an image projected onto the image capture sensor 104. The image capture sensor 104 can be positioned within the body 102 near the chimney 110 (axial below the chimney), but can be connected to other parts of the body 102 and can be external to the body 102 in some examples. In some examples, the image capture sensor 104 can be connected to an integrated circuit board configured to support and electrically connect components, including transistors and circuits of any of multiple forms known in the industry, providing conductive structures and contacts to distribute signals.

The lens assembly 106 can be a device configured to engage the body 102 and can be configured to provide a focused image to the image sensor 104. The lens barrel 116 can be a rigid or semi-rigid body comprised of materials such as one or more of metals, plastics, foams, elastomers, ceramics, composites, or the like. The lens barrel 116 can be substantially cylindrical and can have a dimension (e.g., a diameter) sized for insertion into the chimney bore 112 of the chimney. The optical part or parts 118 can be fixed within the lens barrel 116 and can be made of one or more optical materials such as glass, plastic, or other materials that are light transmitting and optically active for the wavelength band that is used by the camera module 100. The lens optical parts 118 can include one or more optical elements, such as fixed-focal-length lenses, a focal zoom system, combiner lenses, or the like.

The flange 120 can be a flange connected to the barrel 116 and extending radially outward therefrom. The flange 120 can be positioned between proximal and distal ends of the lens barrel 116. The flange 120 can be sized and shaped to be secured to the distal portion 114 of the chimney 110, such as by using adhesive (or glue) 122. The adhesive 122 can be any suitable resin, which can be one or more resins chosen from an epoxy resin, an acrylic resin, an acrylate resin, a cyanoacrylate resin, cyano-urethane resin, a polysiloxane resin, or the like.

Further details, assembly, and operation of similar camera modules is discussed below with respect to FIGS. 2-6.

Figure 2:
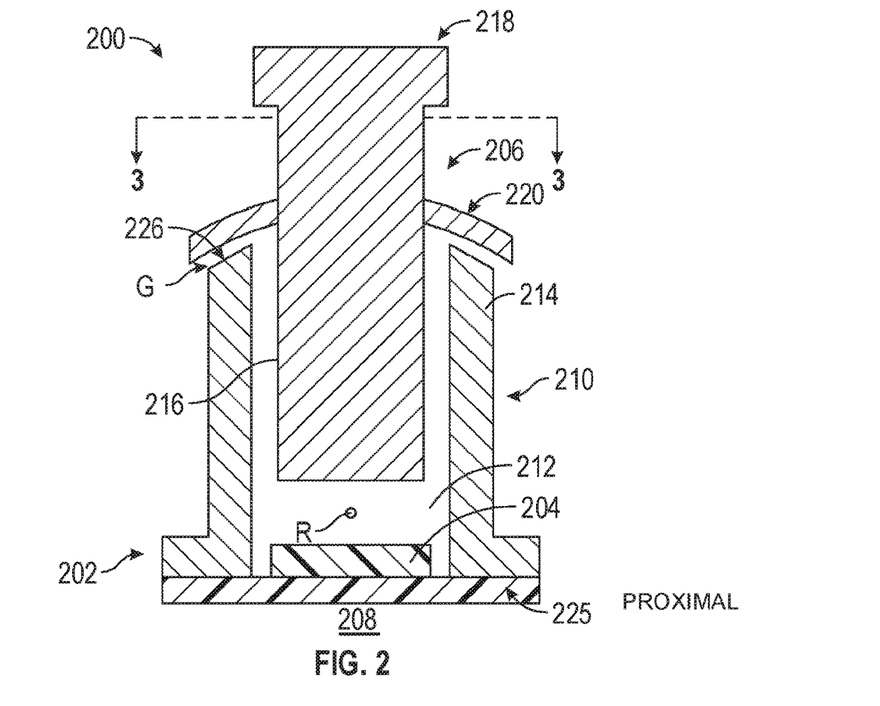
FIG. 2 illustrates a cross-sectional view of a camera module, in accordance with at least one example of this disclosure.

FIG. 2 illustrates a cross-sectional view of a camera module 200, in accordance with at least one example of this disclosure. The camera module 200 can include a chimney having a distal portion that is substantially spherical to help limit asymmetry of an adhesive gap between the flange and the chimney. Any of the previously (or later) discussed camera modules can include such a chimney.

The camera module 200 can include a body 202, an image capture sensor 204, and a lens assembly 206. The body 202 can include a cavity 208 and a chimney 210. The chimney 210 can include a chimney bore 212 and a distal portion 214. The lens assembly 206 can include a lens barrel 216, an optical part 218, and a flange 220. The camera module 200 can also include a board 225. FIG. 2 also shows orientation indicators Proximal and Distal, adhesive gap G, rotational center R, and perspective indicators 3-3.

The components of the camera module 200 can be similar the components of the camera module 100 except that the camera module 200 shows that the image capture sensor 204 can be connected to the board 225 where the board 225 can abut the body 202 to position the image capture sensor 204 near or within the chimney 210.

The camera module 200 can also differ in that the distal portion 214 of the chimney 210 can be substantially spherical or have a substantially spherical profile. In some examples, the distal portion 214 can be curved in one or more directions without being substantially spherical. In some examples, the distal portion 214 can be spherical. Similarly, the flange 220 can be substantially spherical or have a substantially spherical profile. In some examples, the flange 220 can be curved in one or more directions without being substantially spherical. In some examples, the flange 220 can be spherical.

The distal portion 214 and the flange 220 can be shaped such that the distal portion 214 and a proximal surface 226 of the flange 220 are concentric, or substantially concentric, such that rotation (or tilt) of the lens assembly 206 about the rotational center R does not affect the adhesive gap G between the distal portion 214 and the flange 220. More specifically, the distal portion 214 and the flange 220 can allow the lens assembly 206 (and the flange 220) to be rotated about the center of rotation R with respect to the chimney 210 without affecting the adhesive gap G between the chimney 210 and the flange 220, such that the adhesive gap G is substantially constant around a gluing area (or adhesive area) of the of distal portion 214. This design allows for an optical axis of the optical part 218 to be aligned with a mechanical axis of the chimney while maintaining a substantially constant thickness of adhesive between the chimney 210 and the flange 220 to help minimize movement of the optical part 218 with respect to the image capture sensor 204, helping to improve image quality using relatively lower cost lenses, as discussed in further detail below.

The substantially constant adhesive gap G between the chimney 210 and the flange 220 can be, for example 1 millimeter, and in other examples constant at a distance of 0.1 millimeter to 5 millimeters. The substantially constant adhesive gap G between the chimney 210 and the flange 220 can also be, for example an average gap G of 0.5 millimeters to 3 millimeters with a variation of less than 0.01 millimeters. In some examples the variation can be between 0.001 millimeters and 0.1 millimeters.

Figure 3:
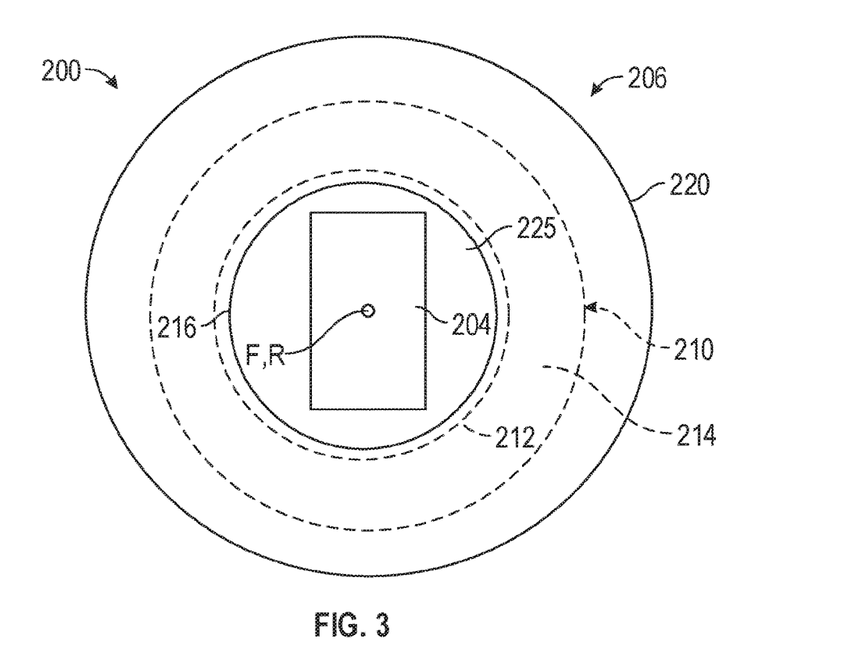
FIG. 3 illustrates a top cross-sectional view of a camera module, in accordance with at least one example of this disclosure.

FIG. 3 illustrates a top cross-sectional view of the camera module 200, in accordance with at least one example of this disclosure. FIG. 3 shows the image capture sensor 204 and the board 225. FIG. 3 also shows the chimney bore 212 and the distal portion 214 of the chimney 210 (shown in phantom). FIG. 3 further shows the lens barrel 216 and the lens flange 220 of the lens assembly 206. FIG. 3 also shows a focal point F and a rotational center R, together indicated by reference character F, R.

The camera module 200 of FIG. 3 can be consistent with the camera module 200 of FIG. 2; FIG. 3 shows additional details of the camera module 200. For example, FIG. 3 shows how the flange 220 can extend radially outward from the lens barrel 216 such that the flange 220 can have a substantially spherical profile with an opening for the lens barrel 216 therethrough (a truncated spherical shape with a bore therethrough). FIG. 3 also shows how the flange 220 can be positioned over the chimney 210 and how the flange 220 can extend radially beyond the chimney 210, which allows the flange 220 to move with respect to the chimney 210 while still providing radial overlap between the flange 220 and the chimney 210.

Figure 4A:
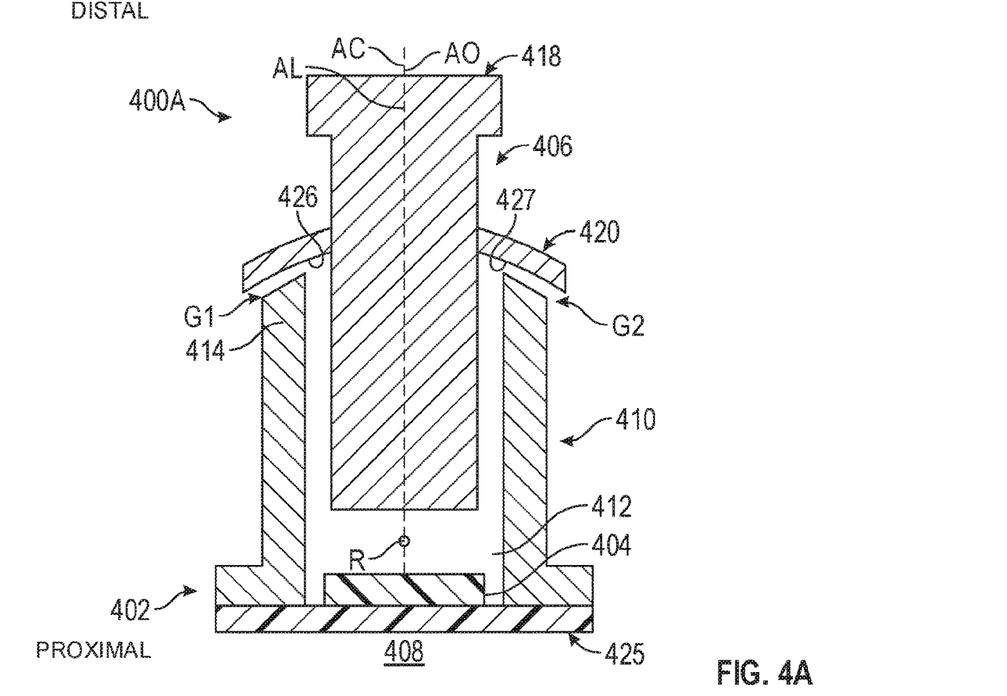
FIG. 4A illustrates a cross-sectional view of a camera module in a first arrangement, in accordance with at least one example of this disclosure.
Figure 4B:
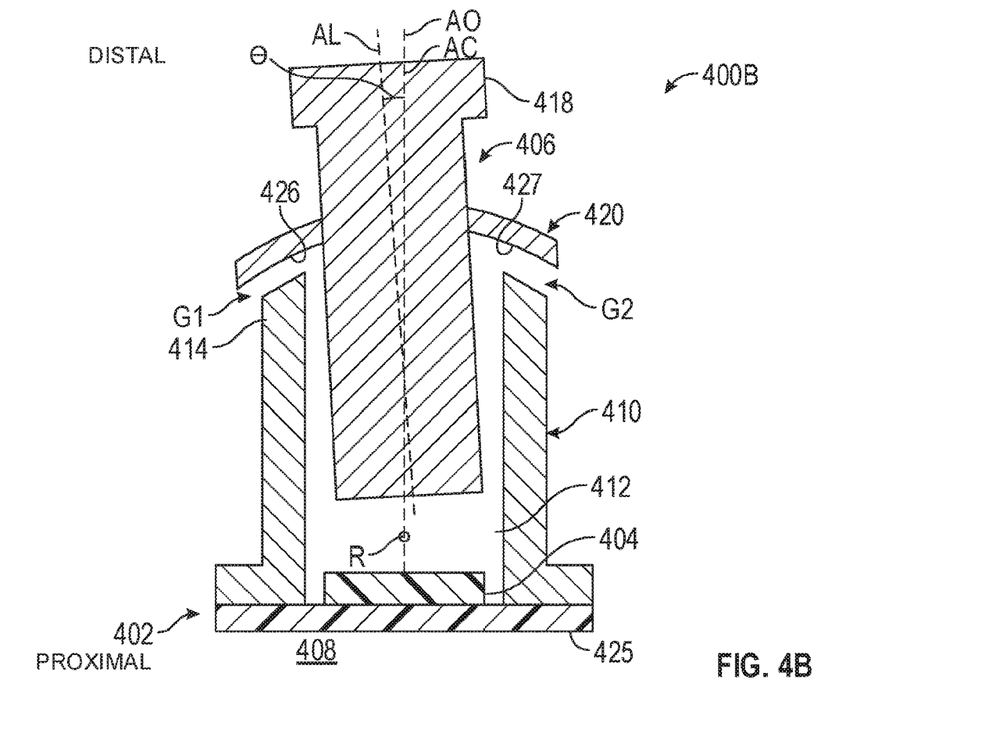
FIG. 4B illustrates a cross-sectional view of a camera module in a second condition, in accordance with at least one example of this disclosure.

FIG. 4A illustrates a cross-sectional view of a camera module 400A in a first arrangement, in accordance with at least one example of this disclosure. FIG. 4B illustrates a cross-sectional view of a camera module 400B in a second condition, in accordance with at least one example of this disclosure. Each of the camera modules 400A and 400B can be consistent with the camera module 200 discussed above with respect to FIGS. 2 and 3; FIGS. 4A and 4B show camera modules with lenses having different focal axes and in different orientations with respect to the bodies of the module. FIGS. 4A and 4B are discussed below concurrently.

Each of the camera modules 400A and 400B can include a body 402, an image capture sensor 404, and a lens assembly 406. The body 402 can include a cavity 408 and a chimney 410. The chimney 410 can include a chimney bore 412 and a distal portion 414. The lens assembly 406 can include a lens barrel 416, an optical part 418, and a flange 420. The camera module 400 can also include a board 425. FIGS. 4A and 4B also shows orientation indicators Proximal and Distal, adhesive gaps G1 and G2, a rotational center R, a lens mechanical axis AL, a chimney mechanical axis AC, a lens optical axis AO, and an angle θ.

The camera module 400A shown in FIG. 4A has a lens mechanical axis AL, a chimney mechanical axis AC, and a lens optical axis AO where each of these axes are substantially in alignment. As such, the lens assembly 406 is not tilted with respect to the chimney 410 and the adhesive gaps G1 and G2 are substantially even and constant around an adhesive area of the distal portion 414 of the chimney 410. However, the optical part 418 of the camera module 400B, shown in FIG. 4B, has an optical axis AO that is not in alignment with the lens mechanical axis AL, such that the lens optical axis AO is rotated (or tilted) by the angle θ with respect to the lens mechanical axis AL. The angle θ between the lens optical axis AO and the lens mechanical axis can be between 0 degrees and 2 degrees in some examples, can be between 0 degrees and 1 degree in some examples, and can be between 0 degrees and 0.5 degrees in some examples. Further by way of example, the angle θ between the lens optical axis AO and the lens mechanical axis can depend on a tolerance of the lens. The tolerance of the lens may be dictated by manufacturing procedures and quality.

As discussed above, this misalignment causes defocus at off-center positions with respect to the image sensor 404, which can cause image focus issues. To help limit image focus issues, the lens assembly 406 can be tilted (or rotated) with respect to the chimney 410 such that the lens optical axis AO aligns with the chimney mechanical axis AC and become perpendicular to the plane of the image capture sensor 404. To align the lens optical axis AO with the chimney mechanical axis AC, the lens mechanical axis AL is rotated about the rotational center R, which causes a rotation of the lens mechanical axis AL with respect to the chimney mechanical axis AC by the angle θ.

In the prior art, such rotation of a lens assembly can cause deviations in the adhesive gaps G1 and G2 (and generally about the adhesive area of a distal portion of a chimney). However, in the camera module 400, because the distal portion 414 of the chimney 410 is substantially spherical and because the flange 420 is substantially spherical and complimentary to the distal portion 414 of the chimney 410 such that the distal portion 414 of the chimney 410 is concentric with the flange 420, the lens assembly 406 can be rotated about the rotational center R to create the angle θ and align the lens optical axis AO with the chimney mechanical axis AC without affecting the adhesive gaps G1 and G2.

That is, when the lens assembly 406 is tilted with respect to the chimney 410 such that the lens optical axis AO is aligned with the chimney mechanical axis AC and the lens mechanical axis AL is offset by the angle θ with respect to the chimney mechanical axis AC, the adhesive gaps G1 and G2 can be substantially the same and can be substantially constant about the adhesive area of the distal portion 414 of the chimney 410. This consistency in adhesive gaps G1 and G2 can help limit differences in a thickness of adhesive disposed between the flange 420 and the chimney 410, which can help reduce asymmetric shrinkage of the adhesive during curing, to help keep the focal point of the optical part 418 in the center of (or in a desired position with respect to) the image capture sensor 404, thereby helping to reduce image focus issues.

As discussed above, the adhesive gaps G1 and G2 can be substantially the same and can be substantially constant about the adhesive area of the distal portion 414 of the chimney 410. That is, the adhesive gaps G1 and G2 can be constant, for example 1 millimeter, and in other examples constant at a distance of 0.1 millimeter to 5 millimeters. The adhesive gaps G1 and G2 can also be, for example an average of 0.5 millimeters to 3 millimeters with a variation of less than 0.01 millimeters. In some examples the variation can be between 0.001 millimeters and 0.1 millimeters. In another example, the adhesive gaps G1 and G2 can also be, for example an average of 0.4 millimeters to 0.8 millimeters with a variation of plus or minus 200 micrometers or a variation of plus or minor 400 micrometers. In some examples, shrinkage can be between 8 and 20 micrometers.

Figure 5:
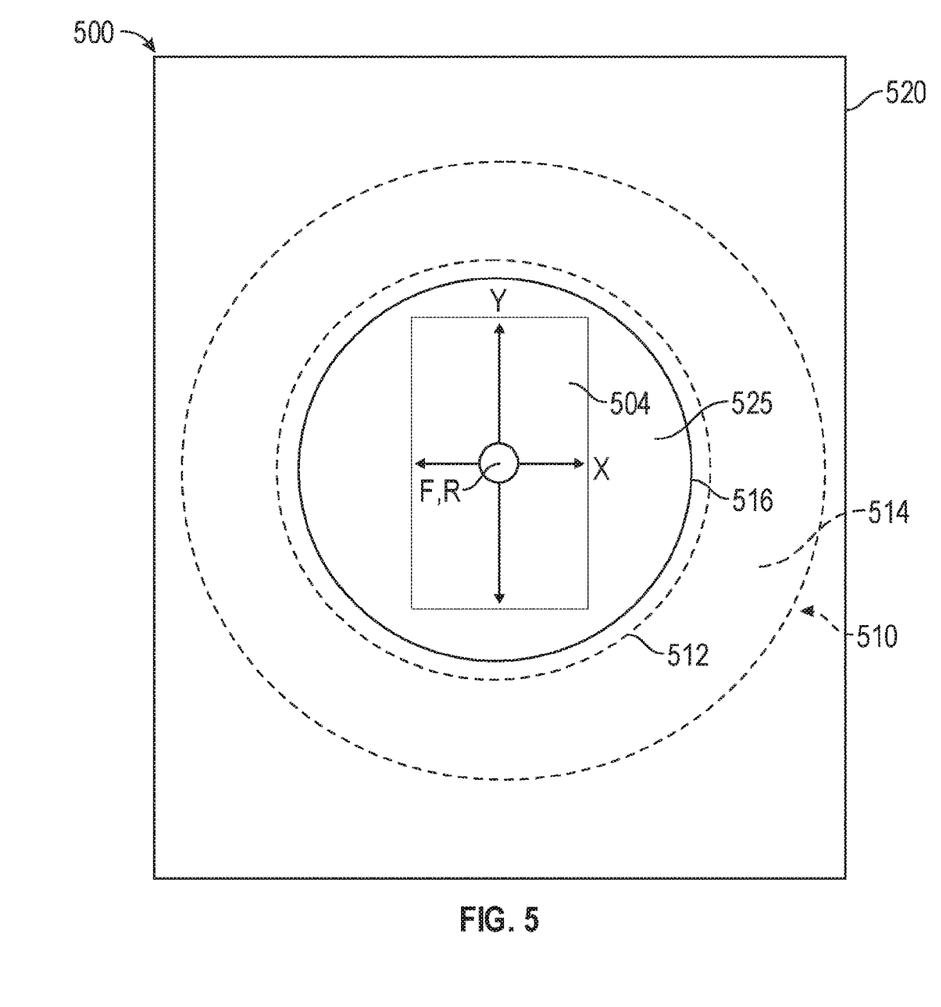
FIG. 5 illustrates a cross-sectional view of a camera module, in accordance with at least one example of this disclosure.

FIG. 5 illustrates a cross-sectional view of a camera module 500, in accordance with at least one example of this disclosure. The camera module 500 can include a chimney having a distal portion that is substantially spherical with a flange that is curved and has a substantially rectangular prism shape. Any of the previously (or later) discussed camera modules can be modified to include such a flange.

FIG. 5 shows the image capture sensor 504 and the board 525. FIG. 5 also shows the chimney bore 512 and the distal portion 514 of the chimney 510 (shown in phantom). FIG. 5 further shows the lens barrel 516 and the lens flange 520 of the lens assembly 506. FIG. 5 also shows a focal point F and a rotational center R, together indicated by reference character F, R, and shows x and y axes.

The camera module 500 of FIG. 5 can be similar to the camera modules 100 and 200 of FIGS. 1-4B, except that the flange 520 of the camera module 500 can have a substantially rectangular prism shape that is curved to be complimentary with the distal portion 514 of the chimney 510.

In some examples, the image capture sensor 504 can have a y axis dimension that is greater than an x axis dimension, such that the image capture sensor 504 is substantially rectangular from the perspective of FIG. 5. Due to the shape of the image capture sensor 504, tilt about the x axis can cause more defocus than tilt about the y axis, because in the y direction there is more off-axis distance. In such a case, the flange 520 can be curved only about the x axis direction. In such a situation a full tilt correction can be applied about the x axis and no tilt (or limited tilt) can be applied about the y axis such that tilt induced defocus and image quality issues due to uneven adhesive shrinkage during curing can be minimized. A lack of curvature of the flange 520 about the y axis means that compensation of the adhesive gap only occurs with tilt of the flange 520 about the x axis; however, because tilt of the lens about the y axis does not affect the image quality as much as tilt about the x axis, a desired focus or image quality can still be achieved. Because manufacturing of a curved cylindrical flange may be relatively less expensive than a substantially spherical flange, the flange 520 of the camera module 500 can provide a relatively low-cost solution to help reduce image quality issues caused by uneven adhesive shrinkage.

In other examples, the flange 520 of the chimney can be designed to compensate for various characteristics of the image capture sensor 504 to achieve a desired focus or image quality result. The flange 520 can be designed to compensate for such characteristics as the surface consistency of the image capture sensor 504 (how planar the surface is), a tilt of the image capture sensor 504 with respect to the chimney 510, manufacturing tolerances of the image capture sensor 504, or the like.

Figure 6:
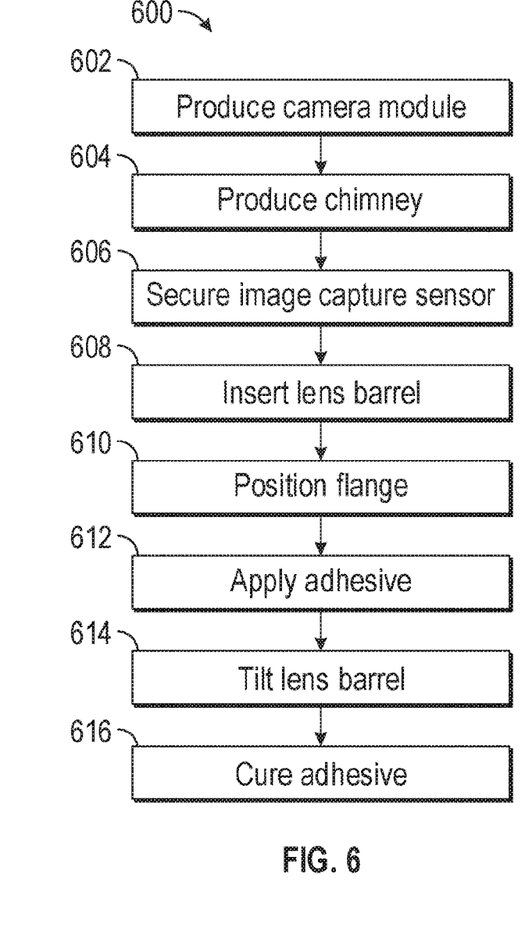
FIG. 6 illustrates a flow chart of an example method, in accordance with at least one example of this disclosure.

FIG. 6 illustrates a schematic view of a method 600, in accordance with at least one example of this disclosure. The method 600 can be a method of manufacturing a portion of a camera module. The steps or operations of the method 600 are illustrated in a particular order for convenience and clarity; many of the discussed operations can be performed in a different sequence or in parallel without materially impacting other operations. The method 600 as discussed includes operations performed by multiple different actors, devices, and/or systems. It is understood that subsets of the operations discussed in the method 600 can be attributable to a single actor, device, or system could be considered a separate standalone process or method.

The method can begin at step 602 where a camera module can be produced, such as the camera module 200 of FIG. 2. At step 604, a chimney can be produced that is couplable to the camera module body such that the chimney extends therefrom, where the chimney can include a distal portion that is substantially spherical. For example, the chimney 210 can be produced that is couplable to the camera module body 202 such that the chimney 210 extends therefrom, where the chimney 210 can include the distal portion 214 that is substantially spherical. At step 606, an image capture sensor can be secured within the body near the chimney, where the image capture sensor can be configured to capture an image delivered thereto. For example, the image capture sensor 204 can be secured within the body 202 near the chimney 210, where the image capture sensor 204 can be configured to capture an image delivered thereto.

At step 608, a lens barrel can be inserted at least partially into the chimney. For example, the lens barrel 216 can be inserted at least partially into the chimney 210. At step 610, a flange of the lens barrel can be positioned adjacent the distal portion of the chimney. For example, the flange 210 of the lens barrel 202 can be positioned adjacent the distal portion 214 of the chimney 210.

In another example, the method 600 can include a step 612 of applying adhesive between the flange and the distal portion of the chimney. In another example, the method 600 can include a step 614 of tilting the lens barrel, such as the lens barrel 216, with respect to the chimney 210 to align an optical axis of a lens located at a distal end of the lens barrel with a mechanical axis of the chimney. The method 600 can also include a step 616 of curing the adhesive.

Notes and Examples

The following, non-limiting examples, detail certain aspects of the present subject matter to solve the challenges and provide the benefits discussed herein, among others.

Example 1 is a camera module comprising: a camera module body; a chimney connected to and extending from the camera module body, the chimney including a distal portion that is substantially spherical; an image capture sensor connected to the body near the chimney and configured to capture an image delivered thereto; and a lens assembly comprising: a lens barrel; an optical device secured to the lens barrel and configured to deliver the image to the image capture sensor; and a flange extending radially from the lens barrel and securable to the distal portion of the chimney.

In Example 2, the subject matter of Example 1 includes, wherein a shape of the chimney is substantially cylindrical with the substantially spherical distal profile end portion at an end of the substantially cylindrical chimney.

In Example 3, the subject matter of Examples 1-2 includes, wherein a shape of the flange is complimentary to the substantially spherical profile of the chimney distal portion.

In Example 4, the subject matter of Example 3 includes, wherein the shape of the flange is substantially spherical and concentric with the substantially spherical profile of the chimney so that a gap between the flange and the distal portion of the chimney is substantially constant between the distal portion of the chimney and the flange when the lens barrel is tilted with respect to the chimney about a center of the substantially spherical profile of the chimney.

In Example 5, the subject matter of Example 4 includes, wherein the tilt of the lens barrel with respect to the chimney is defined by non-coaxial alignment of a mechanical axis of the optical device with respect to a mechanical axis of the chimney.

In Example 6, the subject matter of Example 5 includes, wherein: an optical axis of the optical device is deviated from a mechanical axis of the optical device; and the lens barrel is tilted with respect to the chimney and the image sensor to align the optical axis of the optical device with the mechanical axis of the chimney.

In Example 7, the subject matter of Examples 3-6 includes, wherein the shape of the flange is substantially spherical so that a gap between the flange and the distal portion of the chimney is substantially constant between the distal portion of the chimney and the flange when the lens barrel is tilted with respect to the chimney about a center of the substantially spherical profile of the chimney.

In Example 8, the subject matter of Example 7 includes, wherein the gap between the flange and the distal portion of the chimney is an adhesive gap configured to receive an adhesive therein to secure the flange to the distal portion of the chimney.

In Example 9, the subject matter of Examples 3-8 includes, wherein the shape of the flange and the substantially spherical profile of the chimney are configured to allow for a substantially constant thickness of adhesive between the flange and the distal portion of the chimney when the lens barrel is tilted with respect to the chimney.

In Example 10, the subject matter of Examples 1-9 includes, wherein: the image sensor has a length and a width that is longer than the length; and the flange of the optical device is curved along a direction of the width of the image sensor to substantially match the substantially spherical distal portion of the chimney.

In Example 11, the subject matter of Example 10 includes, wherein the flange of the optical device has a shape of a substantially rectangular prism that is curved.

In Example 12, the subject matter of Example 11 includes, wherein the optical device is fixed with respect to the lens barrel and the flange.

Example 13 is a camera module assembly comprising: a chimney including a distal portion opposite a proximal end, the distal portion having a substantially spherical profile; and a lens assembly comprising: a lens barrel at least partially insertable into the chimney through the distal portion; a optical device secured to a distal end of the lens barrel and configured to deliver the image to an image capture sensor; and a flange extending radially from the lens barrel and securable to the distal portion of the chimney using an adhesive.

In Example 14, the subject matter of Example 13 includes, a camera module body configured to support the chimney such that the chimney extends from the camera module body.

In Example 15, the subject matter of Example 14 includes, wherein the image capture sensor is positioned within the camera module body near the chimney and is configured to capture an image delivered to the image capture sensor by the optical device.

In Example 16, the subject matter of Examples 13-15 includes, wherein a shape of the chimney is substantially cylindrical with the substantially spherical profile end portion at an end of the substantially cylindrical chimney.

In Example 17, the subject matter of Examples 13-16 includes, wherein a shape of the flange is complimentary to the substantially spherical profile of the chimney.

In Example 18, the subject matter of Example 17 includes, wherein the shape of the flange is substantially spherical and concentric with the substantially spherical profile of the chimney so that a gap between the flange and the distal portion of the chimney is substantially constant between the distal portion of the chimney and the flange when the lens barrel is tilted with respect to the chimney about a center of the substantially spherical profile of the chimney.

In Example 19, the subject matter of Example 18 includes, wherein the tilt of the lens barrel with respect to the chimney is defined by non-coaxial alignment of a mechanical axis of the optical device with respect to a mechanical axis of the chimney.

In Example 20, the subject matter of Example 19 includes, wherein: a focal axis of the optical device is deviated from a mechanical axis of the optical device; and the lens barrel is tilted with respect to the chimney and the image sensor to align the focal axis of the optical device with the mechanical axis of the chimney.

Example 21 is a method of manufacturing a camera module, the method comprising: producing a camera module body; producing a chimney couplable to the camera module body such that the chimney extends therefrom, the chimney including a distal portion that is substantially spherical; securing an image capture sensor connected to the body near the chimney, the image capture sensor configured to capture an image delivered thereto; inserting a lens barrel at least partially into the chimney; and positioning a flange of the lens barrel adjacent the distal portion of the chimney.

In Example 22, the subject matter of Example 21 includes, applying adhesive between the flange and the distal portion of the chimney.

In Example 23, the subject matter of Example 22 includes, tilting the lens barrel with respect to the chimney to align an optical axis of an optical device located at a distal end of the lens barrel with a mechanical axis of the chimney; and curing the adhesive.

Example 24 is at least one machine-readable medium including instructions that, when executed by processing circuitry, cause the processing circuitry to perform operations to implement of any of Examples 1-23.

Example 25 is an apparatus comprising means to implement of any of Examples 1-23.

Example 26 is a system to implement of any of Examples 1-23.

Example 27 is a method to implement of any of Examples 1-23.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A camera module comprising:
   a camera module body;
   a chimney connected to and extending from the camera module body, the chimney including a distal portion that defines a substantially spherical profile;
   an image capture sensor connected to the camera module body near the chimney and configured to capture an image delivered thereto; and
   a lens assembly comprising:
      a lens barrel;
      an optical device secured to the lens barrel and configured to deliver the image to the image capture sensor; and
      a flange extending radially from the lens barrel and securable to the distal portion of the chimney;
   wherein a shape of the flange is complimentary to the substantially spherical profile of the distal portion of the chimney; and
   wherein the shape of the flange is substantially spherical and concentric with the substantially spherical profile of the chimney so that a gap between the flange and the distal portion of the chimney is substantially constant between the distal portion of the chimney and the flange when the lens barrel is tilted with respect to the chimney about a center of the substantially spherical profile of the chimney.

2. The camera module of claim 1, wherein a shape of the chimney is substantially cylindrical with the substantially spherical profile of the distal portion at an end of the substantially cylindrical chimney.

3. The camera module of claim 1, wherein the tilt of the lens barrel with respect to the chimney is defined by non-coaxial alignment of a mechanical axis of the optical device with respect to a mechanical axis of the chimney.

4. The camera module of claim 3, wherein:
   an optical axis of the optical device is deviated from a mechanical axis of the optical device; and
   the lens barrel is tilted with respect to the chimney and the image capture sensor to align the optical axis of the optical device with the mechanical axis of the chimney.

5. The camera module of claim 1, wherein the shape of the flange is substantially spherical so that a gap between the flange and the distal portion of the chimney is substantially constant between the distal portion of the chimney and the flange when the lens barrel is tilted with respect to the chimney about a center of the substantially spherical profile of the chimney.

6. The camera module of claim 5, wherein the gap between the flange and the distal portion of the chimney is an adhesive gap configured to receive an adhesive therein to secure the flange to the distal portion of the chimney.

7. The camera module of claim 1, wherein the shape of the flange and the substantially spherical profile of the chimney are configured to allow for a substantially constant thickness of adhesive between the flange and the distal portion of the chimney when the lens barrel is tilted with respect to the chimney.

8. The camera module of claim 1, wherein:
   the image capture sensor has a length and a width that is longer than the length; and
   the flange of the optical device is curved along a direction of the width of the image capture sensor to substantially match the substantially spherical profile of the distal portion of the chimney.

9. The camera module of claim 8, wherein the flange of the optical device has a shape of a substantially rectangular prism that is curved.

10. The camera module of claim 9, wherein the optical device is fixed with respect to the lens barrel and the flange.

11. A camera module assembly comprising:
    a chimney including a distal portion opposite a proximal end, the distal portion having a substantially spherical profile; and
    a lens assembly comprising:
       a lens barrel at least partially insertable into the chimney through the distal portion;

an optical device secured to a distal end of the lens barrel and configured to deliver an image to an image capture sensor; and a flange extending radially from the lens barrel and securable to the distal portion of the chimney using an adhesive;

wherein a shape of the flange is complimentary to the substantially spherical profile of the chimney; and wherein the shape of the flange is substantially spherical and concentric with the substantially spherical profile of the chimney so that a gap between the flange and the distal portion of the chimney is substantially constant between the distal portion of the chimney and the flange when the lens barrel is tilted with respect to the chimney about a center of the substantially spherical profile of the chimney.

12. The camera module assembly of claim 11, further comprising:

a camera module body configured to support the chimney such that the chimney extends from the camera module body.

13. The camera module assembly of claim 12, wherein the image capture sensor is positioned within the camera module body near the chimney and is configured to capture an image delivered to the image capture sensor by the optical device.

14. The camera module assembly of claim 11, wherein a shape of the chimney is substantially cylindrical with the substantially spherical profile of the distal portion located at an end of the substantially cylindrical chimney.

15. The camera module assembly of claim 11, wherein the tilt of the lens barrel with respect to the chimney is defined by non-coaxial alignment of a mechanical axis of the optical device with respect to a mechanical axis of the chimney.

16. The camera module assembly of claim 15, wherein:

a focal axis of the optical device is deviated from a mechanical axis of the optical device; and the lens barrel is tilted with respect to the chimney and the image capture sensor to align the focal axis of the optical device with the mechanical axis of the chimney.

17. A camera module comprising:

a camera module body;

a chimney connected to and extending from the camera module body, the chimney including a distal portion that is a substantially spherical profile;

an image capture sensor connected to the camera module body near the chimney and configured to capture an image delivered thereto; and a lens assembly comprising:

a lens barrel;

an optical device secured to the lens barrel and configured to deliver the image to the image capture sensor; and a flange extending radially from the lens barrel and securable to the distal portion of the chimney;

wherein a shape of the flange is complimentary to the substantially spherical profile of the distal portion of the chimney; and wherein the shape of the flange and the substantially spherical profile of the chimney are configured to allow for a substantially constant thickness of adhesive between the flange and the distal portion of the chimney when the lens barrel is tilted with respect to the chimney.

18. The camera module of claim 17, wherein:

the image capture sensor has a length and a width that is longer than the length; and the flange of the optical device is curved along a direction of the width of the image capture sensor to substantially match the substantially spherical profile of the distal portion of the chimney.

19. The camera module of claim 18, wherein the flange of the optical device has a shape of a substantially rectangular prism that is curved.

20. The camera module of claim 19, wherein the optical device is fixed with respect to the lens barrel and the flange.

* * * * *